US005773498A

United States Patent [19]

Mahood

[11] Patent Number: 5,773,498
[45] Date of Patent: Jun. 30, 1998

[54] DIPHOSPHITES

[75] Inventor: James A. Mahood, Parkersburg, W. Va.

[73] Assignee: General Electric Company, Pittsfield, Mass.

[21] Appl. No.: 774,413

[22] Filed: Dec. 31, 1996

Related U.S. Application Data

[62] Division of Ser. No. 538,372, Oct. 5, 1995, Pat. No. 5,618, 961, which is a continuation of Ser. No. 96,107, Jul. 22, 1993, Pat. No. 5,523,448.

[51] Int. Cl.$^6$ ..................................................... C08K 5/49
[52] U.S. Cl. ..................... 524/119; 252/400.24; 524/128; 524/451; 524/474; 558/78
[58] Field of Search .................................. 524/128, 119, 524/451, 494

[56] References Cited

U.S. PATENT DOCUMENTS

| 3,039,993 | 6/1962 | Friedman | 524/120 |
|---|---|---|---|
| 3,056,823 | 10/1962 | Hecheubleikner et al. | 558/119 |
| 3,264,247 | 8/1966 | Friedman | 524/117 |
| 3,281,381 | 10/1966 | Hecheubleikner et al. | 524/150 |
| 3,305,526 | 2/1967 | Guttag | 528/108 |
| 3,342,767 | 9/1967 | Buckley | 524/117 |
| 3,415,906 | 12/1968 | Shepard et al. | 558/75 |
| 3,437,720 | 4/1969 | Guttag | 528/108 |
| 3,441,633 | 4/1969 | Friedman | 558/78 |
| 3,467,733 | 9/1969 | Dever et al. | 558/78 |
| 3,482,002 | 12/1969 | Dever et al. | 558/78 |
| 3,483,147 | 12/1969 | Freidman | 521/169 |
| 3,488,407 | 1/1970 | Schall et al. | 558/78 |
| 3,509,091 | 4/1970 | Cleveland et al. | 524/117 |
| 3,646,173 | 2/1972 | Gordon et al. | 558/95 |
| 3,714,302 | 1/1973 | Dever et al. | 558/85 |
| 3,794,629 | 2/1974 | Eimers et al. | 524/107 |
| 3,845,168 | 10/1974 | Gattag | 558/78 |
| 4,086,304 | 4/1978 | Hutton et al. | 558/71 |
| 4,118,352 | 10/1978 | Haberlein et al. | 524/387 |
| 4,125,500 | 11/1978 | Mayer et al. | 524/387 X |
| 4,125,501 | 11/1978 | Haberlein et al. | 524/387 X |
| 4,405,739 | 9/1983 | Kinson | 524/117 |
| 4,708,979 | 11/1987 | Pedrazzetti et al. | 524/249 |
| 4,755,546 | 7/1988 | Hecheubleikner et al. | 524/117 |
| 4,782,170 | 11/1988 | Bae et al. | 556/13 |
| 4,882,374 | 11/1989 | Wang et al. | 524/117 |
| 4,956,406 | 9/1990 | Myers et al. | 524/119 |
| 4,957,954 | 9/1990 | Iizuka et al. | 524/102 |

FOREIGN PATENT DOCUMENTS

| A-1 384 809 | 11/1964 | France . | |
| A-30 09 634 | 9/1980 | Germany . | |
| 007144 | 5/1980 | Japan | 524/128 |

*Primary Examiner*—Judy M. Reddick

[57] ABSTRACT

A diphosphite is provided derived from phosphorous trihalide, tetra alkyl hindered bisphenol, and a neoalkyl diol. The phosphites exhibit improved stability and are useful as thermal oxidative stabilizers for thermoplastic compositions.

18 Claims, No Drawings

DIPHOSPHITES

This is a divisional of application Ser. No. 08/538,372 filed on Oct. 5, 1995, U.S. Pat. No. 5,618,961 which is a continuation of application Ser. No. 08/096,107 filed on Jul. 22, 1993, now U.S. Pat. No. 5,523,448.

BACKGROUND OF THE INVENTION

1. Field of the Invention

The invention relates to diphosphites, and more particularly relates to neoalkyl diphosphites.

2. Description of the Related Art

Diphosphites of the formula:

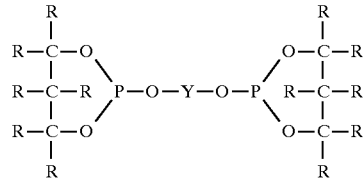

wherein Y is a divalent radical selected from the group consisting of:

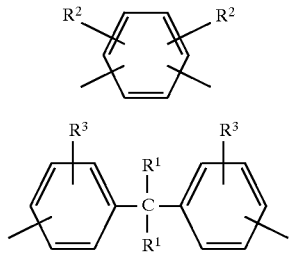

R is independently selected from the group consisting of hydrogen, alkyl of 1 to 6 carbon atoms, preferably of 1 to 4 carbon atoms, and halogen, preferably chlorine or bromine; $R^1$ is independently selected from the group consisting of hydrogen, alkyl of 1 to 12 carbon atoms, preferably from 1 to 6 carbon atoms, $R^2$ is independently selected from the group consisting of hydrogen, alkyl of 1 to 12 carbon atoms, preferably of 1 to 9 carbon atoms, and halogen, preferably chlorine or bromine; and $R^3$ is independently selected from the group consisting of alkyl of 1 to 12 carbon atoms, preferably of 1 to 9 carbon atoms, and halogen, preferably chlorine or bromine, see Dever et al. U.S. Pat. No. 3,467,733 which is incorporated herein by reference. Dever et al. teaches that the diphosphites may be obtained by reacting a cyclic phosphorohalidite of the formula:

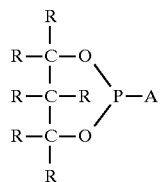

wherein R is as previously mentioned, and A is halogen, preferably chlorine or bromine, and lists 5-butyl-5-ethyl-2-chloro-1,3,2,-dioxaphosphorinane, with a hydroxy organic compound of the formula:

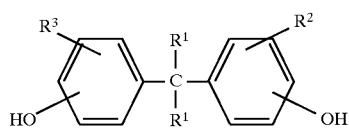

wherein $R^1$, $R^2$, and $R^3$ are as previously mentioned, and lists 2,2-bis(4-hydroxyphenyl) propane among others. While some of these phosphites find utility as stabilizers for polymers, it is desired to improve their hydrolytic and ultraviolet light stability.

Consequently, the present invention provides a diphosphite exhibiting improved stability.

SUMMARY OF THE INVENTION

The present invention provides a phosphite of the formula:

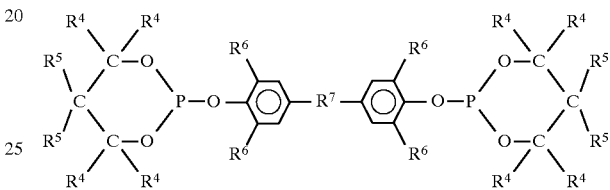

wherein $R^4$, $R^5$, $R^6$ and $R^7$ are as defined below. The diphosphites are useful as stabilizers for organic materials such as thermoplastic polymers and exhibit improved hydrolytic and ultraviolet stability.

DETAILED DESCRIPTION OF THE INVENTION

The diphosphites are represented by the formula:

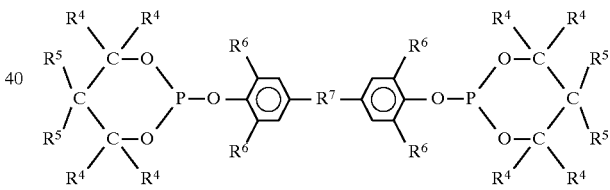

wherein each $R^4$ is independently selected from the group consisting of hydrogen and alkyl radicals of 1 to 6 carbon atoms, preferably of 1 to 4 carbon atoms more preferably hydrogen or t-butyl, and optionally halogen, preferably chlorine or bromine, each $R^5$ is an alkyl group, preferably having from 1 to 6 carbon atoms, each $R^6$ is independently selected from the group consisting of alkyl radicals of 1 to 6 carbon atoms. $R^7$ is a divalent radical, and is preferably a divalent alkylidene having from 1 to 6 carbon atoms such as isoproylidene. Optionally $R^7$ may be a direct bond, or $R^7$ may be a sulphur group or an oxygen group or an organo siloxane group.

The diphosphites may be obtained from the following reactants: a) phosphorous trichloride ($PCl_3$) or a phosphite ester ($P(OR^8)_3$) wherein each $R^8$ is a hydrocarbon radical preferably selected from the group consisting of alkyl and aryl groups, b) neoalkylene glycols, and c) the hydroxy organic compound is tetra alkyl hindered bisphenolic like 2,2-bis(4-hydroxy-3,5-di-t-butyl phenyl) propane. The neoalkylene glycol may be reacted with the phosphorous trichloride to form a phosphorohalidite which can then be reacted with the tetra alkyl hindered bisphenolic such as (2,2-bis(4-hydroxy-3,5-di-t-butyl phenyl)propane) to yield the desired diphosphite.

A nitrogen-containing compound or acid acceptor may be utilized to neutralize the reaction product, there may be utilized triethylamine, tributylamine, tripropylamine, pyridine, dimethylamine, and the like. If desired, a hydrocarbon solvent may be utilized.

The reaction between the cyclic phosphorohalidite and hydroxy organo compound may be effected by mixing the reactants together at room temperature, or, if necessary, by heating the mixture of reactants to moderately elevated temperatures. The reaction can be carried out most conveniently at atmospheric pressures. However, if preferred, pressures either higher or lower than atmospheric may be employed.

Relative amounts of the reactants employed are not critical, although it is desirable that an excess of hydroxy compound be avoided. It is preferred that the cyclic phosphorohalidite and hydroxy organic compound be present in the reaction zone in about stoichiometric proportions.

When a molar proportion of dihydroxy organic compound is reacted, substantially two molar proportions of cyclic phosphorohalidite are employed, however, an excess of up to five or more molar proportions may also be utilized. The nitrogen-containing acid acceptor is added to the reaction product in substantially molar proportions based upon the quantity of cyclic phosphorohalidite utilized. However, it is within the scope of the invention to employ an excess of nitrogen-containing acid acceptor.

In conducting the reaction, the total amount of cyclic phosphorochloridite and hydroxy organic compound may be charged to a reaction vessel initially. The reaction times may vary, but generally time in the range of one to eight hours is sufficient to complete the reaction. Following this initial reaction, the nitrogen-containing acid acceptor may be introduced to the reaction vessel in any suitable manner. The introduction of nitrogen-containing compound is generally completed in times ranging from one to six hours.

The reaction mixture can be worked up in any suitable manner. It is possible, for instance, to remove the solid constituents by filtration. If a solvent is employed in the reaction, it may be removed by distillation, evaporation or by any other suitable method. Because of the high yields which are in many cases obtainable, separation of the desired cyclic diphosphite, following filtration and solvent removal, is not always required for utility of the product and in such cases may be dispensed with. However, if separation is desired, techniques such as distillation, extraction, crystallization, or the like, may be employed.

The diphosphites are useful as stabilizers for polymeric materials including polypropylene, polyethylene, polycarbonate, polyethylene terephthete, polybutylene terephthalate, polyphenylene ethers, polystyrene, acrylonitrile-butadiene-styrene, EPDM rubber, polyurethanes and polyamides. Optionally, the material is a polypropylene, which may contain a residual catalyst such as titanium catalyst on a magnesium halide carrier. The phosphite is preferably present in the polymeric composition at a level of from 0.01 percent by weight to 1 percent by weight based on the total weight of the composition.

Thermoplastic compositions containing a polymer and an amount of the present phosphite can be made by blending. The phosphites of this invention are effective antioxidants which may be employed in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of $\alpha$-olefins, e.g., ethylene, with acrylic or methacrylic acid.

4. Polystyrene.

5. Copolymers of styrene and of $\alpha$-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from $\alpha,\beta$-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polyisobutylene oxide.

13. Polyphenylene oxides.

14. Polyurethanes and polyureas.

15. Polycarbonates.

16. Polysulphones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.

19. Crosslinked polymers which are derived from aldehydes on the one hand and from phenols, ureas and melamines on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyester resins which are derived from copolyesters of saturated and unsaturated dicarboxylic acids with polyhydric alcohols as well as from vinyl compounds as crosslinking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

The phosphites of this invention are particularly effective in stabilizing organic materials such as thermoplastic polymers, in addition to mineral and synthetic fluids such as lubricating oils, circulating oils, etc.

The phosphites of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methylpentene-1), various ethylene-propylene copolymers and the like.

Other polymers in which the phosphites of this invention are particularly useful are polystyrene, including impact polystyrene, ABS resin, SBR, isoprene, as well as natural rubber, polyesters including polyethylene terephthalate and polybutylene terephthalate, including copolymers. Other suitable polymers include polyurethanes, polycarbonates, polyamides such as nylon 6, 6/6 and the like as well as copolyamides and polysulfones.

The phosphites may be used with primary stabilizers such as phenolic antioxidants, a neutralizer such as calcium stearate, pigments, colorants or dyes, UV absorbers, light stabilizers such as hindered amines, metal deactivators, talc and other fillers, etc. Preferably the phosphites should be used in polymeric compositions in combination with a phenolic antioxidant and a neutralizer.

In general, the phosphites of this invention are employed at from about 0.01 to about 5% by weight based on the total weight of the stabilized thermoplastic composition, although this will vary with the particular polymer and application. An advantageous range is from about 0.05 to about 2% by weight thereof, and especially 0.1 to 1% by weight thereof.

The phosphites of this invention stabilize polymers especially during high temperature processing with relatively little change in color, even though the polymer may undergo a number of extrusions. Among the polymers in which this property is especially important are polypropylene, polyethylene, styrenics such as ABS, polyethylene- and polybutylene-terephthalates, polycarbonates, natural rubber, synthetic rubber such as SBR. These phosphites can be used as process stabilizers for polyolefins in the presence of costabilizers such as phenolic antioxidants. A particularly important property for stabilizers which are trivalent phosphorous esters is resistance to hydrolysis in the presence of moisture in the atmosphere during ambient storage. Hydrolysis of the phosphorous esters during storage frequently results in compounds which are less effective. The phosphites of the present invention exhibit hydrolytic stability. The phosphites of the present invention also exhibit resistance to UV yellowing.

The phosphites of the present invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2,6-dialkylphenols, such as, for example, 2,6-di-tert.-butyl-4-methylphenol, 2-tert-butyl-4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.amylphenol), 4,4'-thio-bis-(6-tert.-butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.butylphenol), 2,6-di-(3-tert.-butyl-5-methyl-2-hydroxybenzyl)-4-methylphenol, 2,2'-methylene-bis-[4-methyl-6 (α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-(3,3-bis-(3'-tert.butyl-4'-hydroxyphenyl)-butyrate).

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonate, such as, for example, dioctadecyl 2,2-bis-(3,5-di-tert.-butyl-2-hydroxybenzyl)-malonates, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-(4-(1,1,3,3-tetramethylbutyl)-phenyl)2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-(bis-β-(3,5-di-t-butyl-4-hydroxyphenyl)-propionyl)-hydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonmediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicylo-(2,2,2)octane.

1.11 Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thio-pentadecanol, trimethylhexanediol trimethylolethane, trimethylolpropane, tris-hydroxyethyl isocyanurate and 4-hydroxymethyl-1-phospha-2,6,7-trioxabicyclo(2,2,2)octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol trimethylhexanediol, trimethylolethane, trimethylolpropane, tris-hydroxyethyl isocyanurate and 4-hydroxymethyl-1-phospha-2,6,7-trioxabicyclo (2,2,2)-octane, especially the tetra-bis ester of pentaerythritol.

1.13 Benzylphosphonates, such as, for example, dimethyl 3,5-di-tert.-butyl-4-hydroxybenzyl-phosphonate, diethyl 3,5-di-tert.-butyl-4-hydroxybenzyl-phosphonate dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the phosphite stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline. Octylated diphenylamine, nonylated diphenylamine, N-phenyl-N'-cyclohexyl-p-phenylenediamine, N-phenyl-N-'-isopropyl-p-phenylenediamine, N,N'-di-sect-octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, di-phenylamineacetone condensation product, aldol-1-naphthylamine and phenothiazine.

2. UV-Absorbers and light-stabilizing agents 2.1 2-(2'-Hydroxyphenyl)-benzotriazoles, e.g. The 5'-methyl-, 3',5'-di-tert.-butyl-, 5'-tert.-butyl-, 5'-(1,1,3,3-tetramethylbutyl)-, 5-chloro-3', 5-di-tert. -butyl-, 5-chloro-3'-tert.-butyl-5'-methyl, 3'-sec.-butyl'5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3,5'-di-tert.-amyl-, 3'-methyl-5'-carbomethoxyethyl- and 5-chloro-3',5'-di-tert.-amyl-derivative.

2.2 2,4-bis-(2'-Hydroxyphenyl)-6-alkyl-s-triazines, e.g. the 6-ethyl-, 6-heptadecyl- or 6-undecyl-derivative. 2.3 2-Hydroxybenzophenones, e.g. the 4-hydroxy-, 4-methoxy-, 4-oxtoxy-, 4-decyloxy-, 4-dodocyloxy-, 4-benzyloxy-, 4,2',4'-trihydroxy- or 2'-hydroxy-4,4'-dimethoxy-derivative.

2.4 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'dodecyloxy-benzoyl)-benzene.

2.5 Esters of optionally substituted benzoic acids, e.g. phenylsalicylate, octylphenylsal icylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6 Acrylates, e.g. α-cyano-β,β-diphenylacrylic acid-ethyl ester or -isooctyl ester, α-carbomethoxy-cinnamic acid methyl ester, α-cyano-β-methyl-p-methoxycinnamic acid methyl ester or -butyl ester or N-(β-carbomethoxyvinyl) -2-methyl-indoline.

2.7 Sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro(4,5)decane-2,4-dione.

2.8 Oxalic acid diamides, e.g. 4,4'-di-octyloxy-oxanilide, 2,2'-di-octyloxy-5,5'-di-tert.-butyl-oxanolide. 2.2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and paramethoxy- as well as of o- and p-ethoxy-disubstituted oxanilides.

3. Metal deactivators, e.g. oxanilide, isophthalic acid dihyrazide, sebacic acid-bis-phenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis(3, 5-di- tert-butyl-4-hydroxyphenylpropionyl)hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilizers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa 3,9-diphospha(5,5)-undecane and tri-(4-hydroxy-3,5-di-tert.butylphenyl) phosphite.

Other additives that can be incorporated in the stabilized compositions are optionally thiosynergists such as dilauryl-thiodiproprionate or distearylthiodipropionate, lubricants such as stearyl alcohol fillers, carbon black, asbestos, lanolin, talc, glass fibers, pigments, optical brighteners, fireproofing agents and antistatic agents.

Polymeric particles may be coated with the present phosphites alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference February 24–27, 1991 and as disclosed in Pedrazzeth et al. U.S. Pat. No. 4,708,979 entitled Process for the Stabilization of Spherically Polymerized Polyolefins, issued Nov. 24, 1987, both of which are disclosed herein by reference. Particle formation may be achieved by support Ziegler-Natta Catalyst systems. Suitable commercial processes are known by the trademarks: Spheripol, Addipol and Spherilene.

EXAMPLES

Phos 1

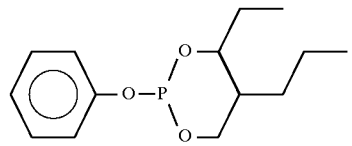

Phos 2

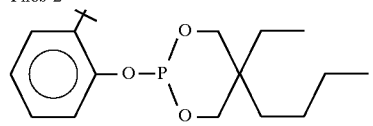

Phos 3

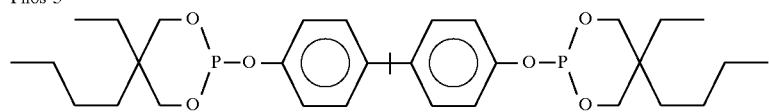

Phos 4

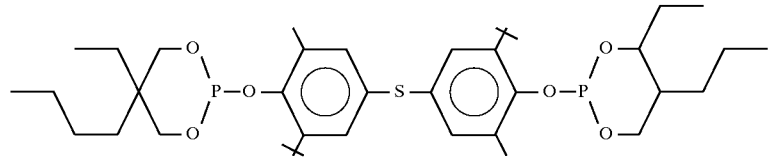

TABLE 1

| Example | Phos   | T½  | UVY |
|---------|--------|-----|-----|
| A       | PHOS 1 | 4   | No  |
| B       | PHOS 2 | 15  | Yes |
| C       | PHOS 3 | 22  | Yes |
| 1       | PHOS 4 | 64+ | No  |

T 1/2 is the in-polymer (polypropylene) hydrolytic stability of the phosphite at 60° C./75% relative humidity in days to loss of 50% of the phosphites. UVY indicates whether the phosphite turned yellow under ultraviolet light. Examples A–C are comparative examples. Example 1 illustrates the enhanced hydrolytic stability and resistance to ultraviolet light yellowing of the phosphite present invention.

I claim:

1. A thermoplastic composition comprising a thermoplastic polymer and a phosphite of the formula

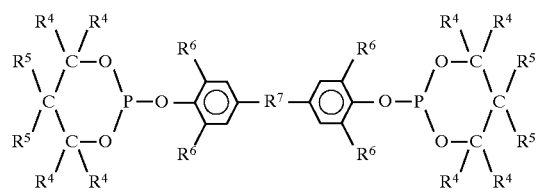

wherein each $R^4$ is hydrogen, each $R^5$ is independently selected from the group consisting of alkyl radicals of one to six carbon atoms, each $R^6$ is a tertiary butyl radical, $R^7$ is a divalent alkylidene radical having from 1 to 6 carbon atoms and wherein said phosphite is present in an amount effective to enhance the thermal oxidative stability of said composition.

2. The composition of claim 1 wherein said phosphite is present at a level of from 0.01 to 1 percent by weight based on the total weight of the composition.

3. The composition of claim 2 wherein said thermoplastic polymer is polypropylene.

4. A thermoplastic composition consisting essentially of a thermoplastic polymer and a phosphite of the formula

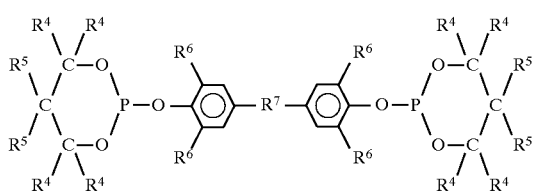

wherein each $R^4$ is hydrogen, each $R^5$ is independently selected from the group consisting of alkyl radicals of one to six carbon atoms, each $R^6$ is a tertiary butyl radical, $R^7$ is a divalent alkylidene radical having from 1 to 6 carbon atoms and wherein said phosphite is present in an amount effective to enhance the thermal oxidative stability of said composition.

5. The thermoplastic composition of claim 1, wherein each $R^5$ is a methyl group.

6. The thermoplastic composition of claim 4, wherein each $R^5$ is a methyl group.

7. The thermoplastic composition of claim 1, wherein the phosphite has the formula:

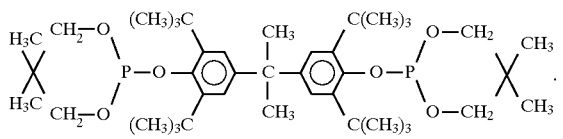

8. The thermoplastic composition of claim 4, wherein the phosphite has the formula:

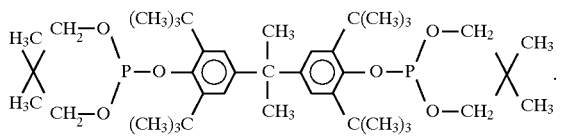

9. The thermoplastic composition of claim 1, wherein the phosphite is present at a level from about 0.01 to about 5% by weight based upon the total weight of the composition.

10. The thermoplastic composition of claim 1, wherein the phosphite is present at a level from about 0.05 to about 2% by weight based upon the total weight of the composition.

11. The thermoplastic composition of claim 1, wherein the thermoplastic resin is a polyolefin resin.

12. The thermoplastic composition of claim 4, wherein the thermoplastic resin is a polyolefin resin.

13. The thermoplastic composition of claim 1, wherein the thermoplastic resin is selected from the group consisting of polystyrene, impact polystyrene, ABS resin, SBR, isoprene, natural rubber, polyesters, polyurethanes, polycarbonates, polyamides, copolyamides, and polysulfones.

14. The thermoplastic composition of claim 4, wherein the thermoplastic resin is selected from the group consisting of polystyrene, impact polystyrene, ABS resin, SBR, isoprene, natural rubber, polyesters, polyurethanes, polycarbonates, polyamides, copolyamides, and polysulfones.

15. The thermoplastic composition of claim 1, further comprising at least one optional additive of the group consisting of thiosynergists, lubricants, carbon black, lanolin, talc, glass fibers, pigments, optical brighteners, fireproofing agents, and antistatic agents.

16. The thermoplastic composition of claim 4, further consisting essentially of at least one optional additive of the group consisting of thiosynergists, lubricants, carbon black, lanolin, talc, glass fibers, pigments, optical brighteners, fireproofing agents, and antistatic agents.

17. The thermoplastic composition of claim 1, further comprising a phenolic antioxidant and a neutralizer.

18. The thermoplastic composition of claim 4, further consisting essentially of a phenolic antioxidant and a neutralizer.

* * * * *